US006846938B2

(12) United States Patent
Leon et al.

(10) Patent No.: US 6,846,938 B2
(45) Date of Patent: Jan. 25, 2005

(54) WATER-COMPATIBLE EPOXY COMPOUNDS CONTAINING SULFONATE OR THIOSULFATE MOIETIES

(75) Inventors: Jeffrey W. Leon, Rochester, NY (US); Robert E. McCovick, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 176 days.

(21) Appl. No.: 10/207,297

(22) Filed: Jul. 29, 2002

(65) Prior Publication Data

US 2004/0019173 A1 Jan. 29, 2004

(51) Int. Cl.$^7$ ............................................ C07D 303/00
(52) U.S. Cl. ........................ 549/512; 549/556; 549/562
(58) Field of Search ........................ 523/428; 524/500; 525/108, 114, 118, 162, 163, 189, 327.3, 327.5, 333.9, 350, 396, 397; 549/200, 512, 514, 515, 516, 543, 554, 556, 562

(56) References Cited

U.S. PATENT DOCUMENTS

| | | | |
|---|---|---|---|
| 3,619,398 A | 11/1971 | Bosso et al. | |
| 3,839,252 A | 10/1974 | Bosso et al. | |
| 3,894,922 A | 7/1975 | Bosso et al. | |
| 3,928,156 A | 12/1975 | Wismer et al. | |
| 3,936,405 A | 2/1976 | Sturni et al. | |
| 3,937,679 A | 2/1976 | Bosso et al. | |
| 3,959,106 A | 5/1976 | Bosso et al. | |
| 3,962,165 A | 6/1976 | Bosso et al. | |
| 4,001,101 A | 1/1977 | Bosso et al. | |
| 4,001,156 A | 1/1977 | Bosso et al. | |
| 4,035,275 A | 7/1977 | Sturni et al. | |
| 4,110,287 A | 8/1978 | Bosso et al. | |
| 4,208,262 A | 6/1980 | Kubo et al. | |
| 4,243,772 A | * 1/1981 | Paul et al. ................ | 525/344 |
| 4,379,872 A | 4/1983 | Ishikura et al. | |
| 4,487,674 A | 12/1984 | Jan Al et al. | |
| 5,483,012 A | 1/1996 | Midogohchi et al. | |
| 5,602,193 A | 2/1997 | Stark | |

FOREIGN PATENT DOCUMENTS

GB    1 530 649    11/1978

OTHER PUBLICATIONS

U.S. patent application Ser. No. 10/207,583 "Imaging Members With Ionic Multifunctional Epoxy Compounds" by West et al.
U.S. patent application Ser. No. 10/207,720 "Water–Compatible Cationic Epoxy Compounds" filed on even date herewith, by J.W. Leon et al.
ACS Symp. Ser. # 114, (1978) (Epoxy Resin Chemistry), pp 57–69, by W. Raudenbesch.
M. Wismer et al., *Journal of Coatings Technology*, "Cathodic Elecrodeposition", vol. 54, No. 688, May 1982, pp 35–44.
P.I. Kordomenors et al., *Journal of Coatings Technology*, "Polymer Compositions For Cationic Electrodepositable Coatings", vol. 54, No. 686, Mar. 1882, pp 33–41.
JP Abstract 52 008886B.
Kubota et al. "Colopsinols D and E, New Polyhydroxyl Linear Carbon Chain Compounds from Marine Dinoflagellate Amphidinium sp." *Chem. & Pharm. Bull.* 48, No. 10, 2000, pp 1447–1451.
Kobayashi et al. "Colopsinol A, a Novel Polyhydroxyl Metabolite from Marine Dinoflagellate Amphidinium sp." *J. Org. Chem.* 1999, 64, pp 1478–1482.
Nakamura et al., "Zooxanthellatoxin–A, a Potent Vasoconstrictive 62–Membered Lacone from a Symbiotic Dinoflagellate", *J. Am. Chem. Soc.* 1995, 117, pp 55–551.
Nakamura et al., "Structure of Periodate Oxidation Products with Characteristic Partial Structures of Zooxanthellatoxin–A, a Potent Vasoconstrictive Polyol from a Symbiotic Dinoflagellate" *J. Org. Chem.* 1993, 58, pp. 313–314.

* cited by examiner

Primary Examiner—James J. Seidleck
Assistant Examiner—Thao Tran
(74) *Attorney, Agent, or Firm*—J. Lanny Tucker

(57) ABSTRACT

Water-compatible branched or unbranched epoxy compounds comprise a backbone having covalently attached two or more epoxy moieties and one or more of the same or different sulfonate or thiosulfate moieties.

5 Claims, No Drawings

WATER-COMPATIBLE EPOXY COMPOUNDS CONTAINING SULFONATE OR THIOSULFATE MOIETIES

FIELD OF THE INVENTION

This invention relates to novel compositions of matter. More particularly, it relates to epoxy compounds that are water-soluble or water-dispersible and that contain both epoxy and specific anionic sulfur moieties. These compounds have utility in heat-sensitive compositions and imaging members such as lithographic printing plates.

BACKGROUND OF THE INVENTION

Epoxy resins represent a very broad class of organic materials that have been found useful in a variety of applications both as bulk materials in and of themselves, as components in composite materials, and as crosslinkers for various polymers. A complete discussion of this multi-billion dollar industry and the huge variety of the chemistry and products involving epoxy resins is provided in a very large amount of literature. See, for example, Flick, Ernest W. *Epoxy Resins, Curing Agents, Compounds, and Modifiers. An Industrial Guide*, Noyes Data Corp.: Park Ridge, N.J., 1987 and Bruins, Paul F. *Epoxy Resins Technology*, Interscience: New York, 1968.

Despite the large amount of available epoxy technology, the overwhelming majority of the uses of epoxy resins involve the preparation of an end product (a bulk material or a coating) that is mechanically tough, resistant to the elements, chemical resistant, and very hydrophobic. Thus, known epoxy resins have not found extensive use in hydrophilic environments in which a net hydrophilic, water-swellable, water-compatible, or readily wettable end product is required. Such uses include bio-compatible materials, aqueous separations media, coatings for lithographic printing plates, and photographic materials.

The current global trend of reducing the amounts of volatile organic compounds permitted in industrial emissions has fueled a continuing interest in the development of useful technology for aqueous-based formulations and coatings for many uses including lithography or computer-to-plate imaging members. Consequently, advances in epoxy resin chemistry have allowed for the use of epoxy resins material in aqueous formulations. The most common strategy for the use of such epoxy resins in aqueous formulations has involved the preparation of aqueous dispersions of hydrophobic, water-insoluble epoxy resins. These dispersions are typically stabilized either by a surfactant or a protective colloid such as poly(vinyl alcohol). Many of these dispersions are sold commercially and a representative example of this type of system is described in U.S. Pat. No. 5,602,193 (Stark). These epoxy resins, while dispersible in water, are still largely hydrophobic in nature and are not suitable for the applications noted above wherein the target material or coating must be highly wettable or must have a very high water uptake or water compatibility. These resins are also largely incompatible with many water-soluble polymers and multi-phase formulations may result when they are used.

There are a large number of patents describing cationic epoxy resins of the type that are commonly used in electrophoretic coating processes (also knows as electrodeposition coating). These materials, however, are fundamentally different from negatively charged epoxy materials because they have charged units that are cationic rather than anionic. The differently charged resins will thus have fundamentally different strengths and limitations in coating formulations. Specifically, both classes of resins will have different compatibilities with other formulation components.

Epoxy resins having anionic or zwitterionic moieties are broadly described in ACS Symposium Series # 114 (Epoxy Resin Chemistry), pp. 57–69, (Vol. Date 1978), *Journal of Coatings Technology* Vol. 54, No. 688, pp. 35–44 (1982), *Journal of Coatings Technology* Vol. 54, No. 686, pp. 33–41 (1982), U.S. Pat. No. 3,928,156 (Wismer et al.), and U.S. Pat. No. 4,066,592 (Wismer et al.).

These resins, however, contain carboxylate units as the anionic moieties and are not feasible for use in low pH coating formulations. In addition, it must be noted that the term "epoxy resin" is commonly used to describe materials in the art include compounds that contain epoxy moieties as well as compounds that are derived from epoxy-containing precursors that contain no epoxy moieties. The carboxylate resins described in the prior art are derived from compounds containing epoxy resins. They do not include both carboxylate and epoxy moieties in the same molecule.

Thus, there is a need for epoxy compounds that are not pH sensitive, can be readily formulated and used in hydrophilic (or aqueous environments) and do not lose their ionic charge in coated form.

SUMMARY OF THE INVENTION

This invention provides a water-soluble or water-dispersible, branched or unbranched compound comprising a backbone having covalently attached two or more epoxy moieties and one or more of the same or different sulfonate or thiosulfate moieties.

The epoxy compounds of this invention comprise both epoxy units and certain anionic sulfur moieties that are covalently bound to a backbone. Preferably, the resins are derived from epoxy-containing backbone precursors that contain at least 25% by weight of oxygen with the remainder being aliphatic hydrocarbons and halogens. These precursor compounds are soluble in water or water-miscible solvents. These epoxy compounds prepared therefrom are useful in the formulation of hydrophilic, water-compatible, water-swellable, or water-wettable coatings and materials and have unexpectedly good solution compatibility with oppositely charged polyelectrolytes.

DETAILED DESCRIPTION OF THE INVENTION

As most of the compounds of this invention are polydisperse materials having structures that will vary in degree of branching and the degree of functionalization (pendant moieties), it is implied that all descriptions of chemical compounds will apply to the mean, or average structure of each material. Thus, the compounds of this invention can be linear, partially branched to any degree, or fully branched in structure.

The compounds can be obtained from epoxy-containing "precursor compounds" that are branched or unbranched, monomeric, oligomeric, or polymeric compounds comprising at least 25% by weight of oxygen with the remainder of the weight comprising of aliphatic hydrocarbon and residual aliphatic haloalkyl groups (usually chloroalkyl groups). The oxygen atoms are covalently bound within the precursor compound as hydroxy, aliphatic ether, epoxy, or aliphatic ester moieties. Preferably, all non-epoxy moieties are either hydroxy or aliphatic ether groups. Preferably, the percentage of oxygen (by weight) in the precursor compounds is from about 30% to about 50%. It would be apparent to one skilled in the art that the backbones of the epoxy compounds of this invention and the precursor compounds have essentially the same percentage of oxygen. For purposes of this invention, "backbone" refers to the compounds that result if the sulfonate or thiosulfate moieties are severed from the remainder of the compounds at the carbon-sulfur atom bond connecting the charged moiety and a hydrogen atom is added to provide proper stoichiometry.

In some embodiments, there are no aromatic groups in the backbone of the compounds of this invention (either aromatic carbocyclic or heterocyclic groups).

Furthermore, the precursor compounds are soluble in water or water-miscible solvents such as various alcohols (such as methanol, ethanol, and propanol), tetrahydrofuran, acetonitrile, acetone, glycols (such as ethylene glycol and diethylene glycol), and methyl ethyl ketone.

Preferred precursor compounds are glycidylated carbohydrates and glycidylated polyglycerols. More particularly, representative precursor compounds used to prepare the compounds of this invention are identified below as Precursors I, II, III, and IV, and Precursors I and II are most preferred:

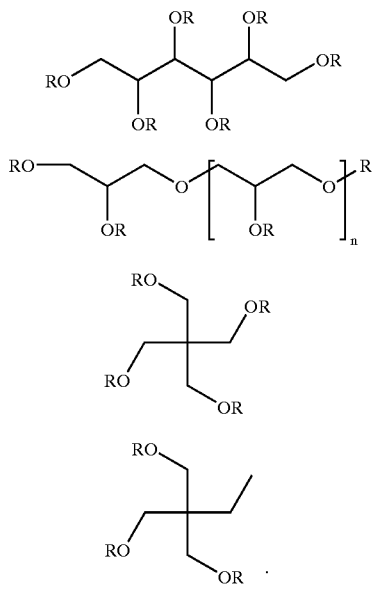

In these compounds, the R groups can be the same or different in each molecule and can be either hydrogen or a glycidyl moiety

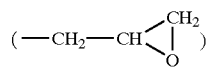

as long as at least two R groups are glycidyl moieties. Furthermore, Precursors I–IV are also intended to represent branched variations of the simplified linear structures that are illustrated as well as oligomeric species that are formed by intermolecular coupling reactions. It should also be noted that certain methods of preparation of the compounds of this invention result in the presence of haloalkyl residues (in particular, R—$CH_2Cl$ groups) as common byproducts. Though these units are not shown in the simplified structures in FIG. 1, their presence in the structures described herein is implied throughout this document and in the descriptions herein.

In Precursor II, n is generally from 1 to 10, and preferably from 2 to 4.

Most preferred precursor compounds include but are not limited to the following materials: glycidyl ethers of sorbitol (Precursor I, sold by Esprit Chemicals under the tradename of CR-5L and by Nagase Chemicals under the tradename of EX-611), of other reduced or non-reduced sugars or polysaccharides, or of cellulosics, polyglycerol glycidyl ethers (Precursor II, sold by Nagase Chemicals under the trademark of Denacol® EX-521 and EX-512), pentaerythritol polyglycidyl ethers (Precursor III, sold by Nagase Chemicals under the trademark of Denacol® EX-313 and EX-314), trimethylolpropane polyglycidyl ethers (Precursor IV), glycerol polyglycidyl ethers, poly(ethylene glycol) diglycidyl ethers, glycidyl ethers of poly(vinyl alcohol), and poly(propylene glycol) diglycidyl ether.

Another common class of materials useful as epoxy-containing precursor compounds are glycidyl ethers and polyglycidyl ethers of bisphenol compounds. These industrially important resins are sold by Shell Chemicals under the EPON brand name. The bisphenol may be, but not necessarily limited to 4,4'-isopropylidenebisphenol, 4,4'-methanebisphenol, 4,4'-sulfonylbisphenol, 4,4'-ethylidenebisphenol, 4,4'-isopropylidenebis(2,6-dimethylphenol), 4,4'-cyclohexylidenebisphenol, 4,4'-(1,4-phenylenediisopropylidene)bisphenol, 4,4'-(1,3-phenylenediisopropylidene)-bisphenol, 4,4'-(1-phenylethylidene)bisphenol, and 1,5-dihydroxynaphthalene. These resins are typically produced by etherification of a polyphenol with epichlorohydrin in the presence of alkali. When more than one equivalent of epichlorohydrin is reacted with each phenol unit, repeating glycerol ether linkages will be present between the phenolic unit and the terminal glycidyl unit. For example, such a resin synthesized from 4,4'-isopropylidenebisphenol will have the following structure, where n is commonly between 0 and 50.

Another class of epoxy-containing compounds useful as precursor compounds includes glycidyl ethers of phenol-formaldehyde resins such as novolacs and resoles.

Other common classes of precursor compounds are polyglycidyl ethers of polyhydric alcohols and polyglycidyl esters of polycarboxylic acids. The former category may be derived from such alcohols as ethylene glycol, diethylene glycol, triethylene glycol, 1,2,6-hexanetriol, glycerol, cyclohexanedimethanol, sorbitol, trimethylolpropane, pentaerythritol, and similar compounds. Examples of the latter category include esters of oxalic acid, succinic acid, pyromellitic acid, mellitic acid, maleic acid, and adipic acid.

The epoxy compounds of this invention generally have an average molecular weight of from about 250 to about 1,000,000 daltons. Preferably, the average molecular weight will be from about 250 to about 200,000 daltons, and more preferably, from about 274 to about 20,000 daltons.

It should be noted that, when a nucleophile is reacted with a glycidyl unit on one of the precursor compounds, substitution occurs most commonly at the least hindered (terminal) oxirane methylene carbon. However, multiple substitutions at other positions can also occur. The precursor compounds described herein are intended to include epoxy resins in which nucleophilic substitution has occurred at either position of the oxirane ring.

As noted above, the compounds of this invention are water-soluble or water-dispersible. The water-soluble compounds are most preferred. By "water-soluble" is meant that at 60° C., a 2% (by weight) solution of the compound yields a clear solution in water from which no more than 5% of the compound can be recovered by filtration. By "water-dispersible" is meant that at least 2% (by weight) of the compound can be dispersed in water at room temperature without the use of an emulsifying agent to provide a two-phase system that exhibits no observable settling of the solid phase or phase separation after one hour.

The compounds of the present invention may be prepared or used as heterogeneous mixtures, and such mixtures may have both water-soluble and water-dispersible fractions.

The epoxy compounds of this invention will contain two or more epoxy moieties and one or more of the noted sulfonate (—SO$_3^-$) or thiosulfate (—SSO$_3^-$) moieties described below. It will be noted that where the compounds include two or more anionic moieties in the same molecule, those moieties can be the same or different. In addition, the compound may contain pendant hydroxyl groups. The compounds can also include appropriate monovalent cations such as hydrogen, alkali metal ions, ammonium ions, alkaline earth metal ions, or any other metal ions readily apparent to a skilled worker in the art.

It is also apparent that the compounds of this invention can have a net negative charge or a net neutral charge if they are zwitterionic in nature. Preferably, the epoxy compounds have a net negative charge.

The most preferred compounds of this invention include sulfate or thiosulfate moieties as represented by the following Structures C, D, E, and F in which the anionic moieties are attached to the compound backbone.

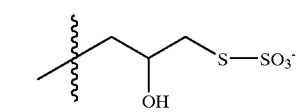

C

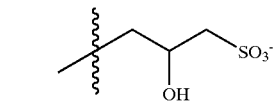

D

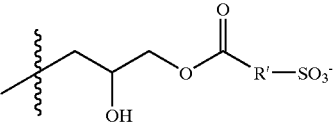

E

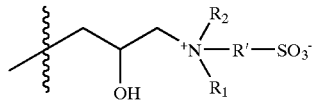

F

In Structures C–G, R', R$_1$ and R$_2$ are defined as follows.

R$_1$ and R$_2$ are independently substituted or unsubstituted alkyl groups having 1 to 12 carbon atoms (such as methyl, ethyl, n-propyl, iso-propyl, hexyl, hydroxymethyl, cyanomethyl, methylenecarboxyalkyl, and dodecyl groups), substituted or unsubstituted carbocyclic or heterocyclic aryl groups having 5 to 10 carbon and/or heteroatoms in the ring (such as phenyl, naphthyl, pyridinyl, tolyl, tetrahydropyranyl, and p-methylphenyl), and substituted or unsubstituted cycloalkyl groups having from 5 to 10 carbon atoms in the carbocyclic ring (such as 1,3- and 1,4-cyclohexyl groups). Alternatively, R$_1$ and R$_2$ can be combined to form a substituted or unsubstituted heterocyclic ring with the charged nitrogen atom, the ring having 4 to 8 atoms in the ring. Such heterocyclic rings include, but are not limited to, substituted or unsubstituted moipholinium, piperidinium, and pyrrolidinium groups. The various groups can also include one or more oxy, thio, carbonyl, amido, or alkoxycarbonyl groups.

Preferred R$_1$ and R$_2$ groups are substituted and unsubstituted alkyl groups having 1 to 3 carbon atoms, and methyl and ethyl groups are more preferred. When R$_1$ and R$_2$ are combined, preferably, they are combined to form morpholinium or piperidinium groups.

In addition, R$_1$ and R$_2$ can contain additional sulfonate or thiosulfate groups as substituents, thereby giving a pendant group with a net charge of −2.

R' can be any divalent linking group (substituted or unsubstituted) that includes one or more carbon atoms and one or more heteroatoms such as oxygen, nitrogen, and sulfur atoms in the linking chain sufficient to link the carbonyl group (in the case of Structure E) or the quaternary ammonium nitrogen (in the case of Structure F) to the sulfonate or thiosulfate group. The linking group can include one or more divalent acyclic or cyclic groups such as aliphatic groups, arylene groups, or heterocyclic groups, in any combination, and any heteroatom linking groups such as oxy, thio, amido, carbonyl, carbonyloxy, sulfonamido, and others readily apparent to one skilled in the art that are chemically possible in such compounds. For Structures E and F, the preferred linking groups are substituted or unsubstituted alkylene groups having 1 to 5 carbon atoms. More preferably, for Structure E, the linking group is methylene and for Structure F, the linking groups are unsubstituted alkylenes having 2 to 5 carbon atoms.

While the compounds of this invention will contain one or more or the same or different anionic moieties and two or more epoxy moieties, preferably, the molar ratio of epoxy moieties to anionic moieties is from about 19:1 to about 1:19. More preferably, this molar ratio will range from about 4:1 to about 1:4.

The epoxy compounds of this invention are synthesized by the reaction of a nucleophilic reagent with the epoxy-containing precursor compound. The amount of the nucleophilic compound will be such that complete conversion will afford a desired product that will contain at least two epoxy moieties and at least one anionic moiety per average molecule. Reaction temperatures will typically range from room temperature to 100° C. More commonly, the temperature will range from about 40° C. to about 60° C. The reactions will typically be run at from about 5% to about 90% solids. It has been found, however, that at 10–20% solids and temperatures of less than 60° C., excellent conversions (yields) can be attained with minimal growth of molecular weight and very little, if any, gelation. The reaction can be conveniently monitored by observing the disappearance of the oxirane protons using proton NMR, by monitoring the disappearance of the nucleophilic compound by ion chromatography, or by measuring a change in pH. The product compound can be stored and used in solution in the reaction solvent. Alternatively, the solvents can be stripped under vacuum to afford the desired compound or the pure compound can be isolated by precipitation into a nonsolvent. The solvent system used may be water or a combination of water and any water-miscible solvents sufficient to solubilize the product compound and allow for at least marginal solubility of the reactants. Water-methanol is a preferred solvent combination.

To yield an epoxy compound comprising thiosulfate moieties (Structure C noted above), an epoxy-containing precursor compound can be reacted with the thiosulfate salt of an inert cation. The thiosulfate salt will preferably be sodium, potassium, or a quaternary ammonium thiosulfate. As the reaction progresses, the pH of the reaction mixture will rise. Thus, the extent of reaction can be easily monitored using a pH meter. A protic acid, in an amount equimolar to the thiosulfate, will need to be gradually added over the course of the reaction. Any acid with a relatively non-nucleophilic anion can be used for this purpose but hydrochloric acid is preferred. A byproduct of this reaction will be the resultant salt of the anion of the added acid with the cation of the thiosulfate. If needed, the product compound can be purified by the evaporation of the solvents under reduced pressure, followed by redissolution in an organic solvent (such as methanol). In most cases, the salt can then be filtered out as an undissolved solid. The resulting compounds can also be identified as "Bunte" salts.

To yield an epoxy compound functionalized with a sulfonate unit (Structure D noted above), an epoxy-containing precursor compound can be reacted with the bisulfite salt of an inert cation. The bisulfite salt will preferably be sodium, potassium, or a quaternary ammonium bisulfite. As bisulfite is a weaker nucleophile than thiosulfate, it is often useful to add an iodide salt (about 5–25 mol % based on bisulfite) as a catalyst. The resulting iodide salt can be removed in the same manner as described for the removal of salts from the thiosulfate-containing compounds. This reaction can be conveniently monitored by the change in pH. For a typical reaction in 1:1 methanol-water of approximately 10–20% solids, the pH will change from about 5 to about 9–11 as the reaction progresses. Alternatively, a sulfite salt can be used as the nucleophile and one equivalent of a protic acid can be added to control the rise in pH as the reaction progresses.

In another synthetic embodiment, an epoxy precursor compound can be reacted via the method described above with a compound containing a sulfonic acid or sulfonate salt linked to a tertiary amine or a nitrogen-containing heterocycle. Examples of such compounds are morpholinoethane sulfonic acid (and the conjugate bases thereof) and pyridinoethane sulfonic acid (and the conjugate base thereof, 2 and 4 isomers). Such a reaction will provide a zwitterionic compound in which the sulfonate group is linked to the backbone by quaternary ammonium or positively charged nitrogen heterocycle unit and any number of other linking and spacer groups (such as alkyl, ester, or amide) to provide a compound that contains pendant $R_1$ and $R_2$ groups as shown in Structure F noted above. The linking group R' is identified above and can comprise any combination of chemical units (such as linear or cyclic alkyl, aryl, ether, thioether, ester, or amide groups, etc.) sufficient to covalently connect the sulfonate to the nitrogen of the quaternary ammonium or heterocycle moiety.

In yet another embodiment, an epoxy precursor compound is reacted via the method described above with a compound containing a sulfonate linked to a carboxylic acid. An example of such a compound is 3-sulfopropionic acid and its conjugate bases. Such a reaction will afford a compound in which the sulfonate group is linked to the backbone by an ester linkage to afford a compound that contains pendant groups shown in Structure E (noted above). The linking group R' is defined above.

It is also possible to prepare and use a mixture of two or more water-soluble or water-dispersible, branched or unbranched compounds of this invention. The compounds would comprise the same or different backbones, each backbone having covalently attached thereto, two or more epoxy moieties and one or more of the same or different sulfonate or thiosulfate moieties. This mixture of compounds can be prepared by reacting a mixture of precursor compounds noted above with the appropriate amounts and types of reactants, depending upon the reaction scheme that is used. The mixture of compounds can be isolated or used in solution. Preferably, in such mixtures, all of the epoxy compounds have a net negative charge.

The following examples are provided to illustrate the practice of this invention and are not meant to be limiting in any way.

PREPARATIVE EXAMPLE 1
Epoxy Compound 1 Containing 3.3 Epoxy Moieties for Every 3.0 Thiosulfate Moieties (Structure C Compound)

DENACOL® EX-521 epoxy resin (20.0 g, Nagase Chemicals) was combined with 115 ml of methanol in a 250 ml 2-neck round bottom flask fitted with a reflux condenser and a nitrogen inlet. Sodium thiosulfate pentahydrate (14.9 g) was added all at once and 1.0 N methanolic hydrochloric acid (20 ml) was added via the addition funnel as needed whenever the pH exceeded 11.5. The addition was completed over 45 minutes. The reaction mixture was allowed to stir for an additional hour at 40° C. A white precipitate (NaCl) was removed by filtration and the desired product was stored as a solution of 19.7% solids in methanol with a final pH of 11.6. Analysis by $^1$H NMR spectrum showed a decrease in the integration of the oxirane protons at $\delta$ 2–5–2.8 ppm, proportional to the amount of thiosulfate added.

PREPARATIVE EXAMPLE 2
Epoxy Compound 2 Containing 3.3 Epoxy Moieties for Every 3.0 Sulfonate Moieties (Structure D Compound)

DENACOL® EX-521 epoxy resin (20.0 g, Nagase Chemicals) was combined with 27.5 ml of methanol, 82.5 g of water, 6.2 g of sodium bisulfite, and 1.6 g of lithium iodide in a 250 ml 2-neck round bottom flask fitted with a reflux condenser and a nitrogen inlet. The reaction mixture was bubble degassed with nitrogen for 10 minutes and stirred for 16 hours at 50° C., at which point the pH had changed from 7.8 to 11.0. The solvents were stripped by rotary evaporation and the clear oil was redissolved in methanol. A small amount of a white powder (LiI) was filtered off and the desired product was stored as a solution in methanol at 15.7% solids. Analysis by $^1$H NMR showed a decrease in the integration of the oxirane protons proportional to the amount of bisulfite added and the appearance of a broad, multimodal peak at $\delta$ 62.95–3.18 ppm pertaining to protons adjacent to the newly introduced sulfonate moieties. In addition, analysis of the product by $^{13}$C NMR showed the appearance of a new peak at δ 55.01 pertaining to the carbons adjacent to the newly introduced sulfonate moieties.

PREPARATIVE EXAMPLE 3

Epoxy Compound 3 Containing 3.3 Epoxy Moieties for Every 3.0 Sodiosulfoacetate Ester Moieties (Structure E Compound)

DENACOL® EX-622 epoxy resin (20.0 g, Nagase Chemicals) was combined with 40 g of methanol, 8.4 g of sulfoacetic acid was dissolved in 120 of 1.0 N aqueous sodium hydroxide to yield a solution of the completely neutralized salt. The two solutions were combined in a 250 ml 2-neck round bottom flask fitted with a reflux condenser and a nitrogen inlet. The reaction mixture was heated overnight at 45° C. (about 16 hours). During that time, 60 ml of 1.0 N methanolic HCl was added over the first 10 hours using a solvent pump. The reaction mixture was allowed to stir at room temperature for an additional 24 hours to yield a product solution with a final pH of about 7–8. The solvents were stripped by rotary evaporation and an attempt was made to dissolve the concentrates in methanol. The desired product was found to be completely insoluble in methanol but could be dissolved in 3:1 methanol:water. By dissolving the desired product in this solvent mixture and filtering, most of the residual salts were removed by filtration. Analysis of the desired product by $^1$H NMR showed the expected stoichiometric decrease in the integration of the oxirane protons, and the appearance of a peak at δ 3.78 ppm corresponding to the methylene protons between the sulfonate and ester functionalities. An IR spectrum (neat, attenuated total reflectance) of the desired product showed a single, unimodal peak in the carbonyl region with a frequency of 1728 cm$^{-1}$. The product was stored as a crude solution of 19.21% solids.

PREPARATIVE EXAMPLE 4

Epoxy Compound 4 Containing 3.3 Epoxy Moieties for Every 3.0 4-Pyridiniumethane Sulfonate Moieties (Structure F Compound)

DENACOL® EX-622 epoxy resin (20.0 g, Nagase Chemicals) was dissolved in 75 ml of methanol. 4-Pyridineethane sulfonic acid (11.2 g) was dissolved in 20 ml of 3.0 N sodium hydroxide to yield a solution of the neutralized salt. The two solutions were combined in a 250 ml 2-neck round bottom flask fitted with a reflux condenser and a nitrogen inlet. The reaction mixture was heated for 6 hours at 45° C. During that time, 60 ml of 1.0 N methanolic HCl was added using an addition funnel at such a rate to maintain the pH at about 7. The final desired product had a greenish color, presumably from the formation of a small amount of conjugated by-product formed via deprotonation of the acidic 4-methylene moiety on the pyridinium moiety. The solvents were stripped using rotary evaporation and the resulting oil was redissolved in methanol and filtered to remove insoluble NaCl. The resulting product was stored as a solution of 24.1% (w/w) in methanol. Analysis by $^1$H NMR showed the expected stoichiometric decrease in the integration of the oxirane protons, and the appearance of two broad peaks at δ 7.93–8.24 and 8.75–9.01 ppm with the expected integration pertaining to the aromatic pyridinium protons.

PREPARATIVE EXAMPLE 5

Epoxy Compound 5 Containing 3.3 Epoxy Moieties for Every 3.0 4-Morpholiniumethane Sulfonate Moieties (Structure F Compound)

DENACOL® EX-622 epoxy resin (20.0 g, Nagase Chemicals) was dissolved in 50 ml of deionized water. 4-Morpholinoethane sulfonate acid (11.8 g) dissolved in 60 ml of 1.0 N sodium hydroxide to yield a solution of the neutralized salt. The two solutions were combined in a 250 ml 2-neck round bottom flask fitted with a reflux condenser and a nitrogen inlet. The reaction mixture was heated for 24 hours at 45° C. Over the first 10 hours, 60 ml of 1.0 N methanolic HCl was added using a solvent pump. The desired product solution had a final pH of about 8. The solvents were stripped via rotary evaporation and the resulting oil was redissolved in methanol and filtered to remove insoluble NaCl. The resulting product was stored as a solution of 19.25% (w/w) in methanol. Analysis by $^1$H NMR showed the expected stoichiometric decrease in the integration of the oxirane protons, and the appearance of an intense peak at δ 3.3–3.4 ppm with the expected integration pertaining to the methylene protons adjacent to the quaternary nitrogen.

PRACTICAL EXAMPLE 1

Heat-Sensitive Printing Plates Containing Epoxy Compounds 1 and 2

It is known in the art of lithographic printing that it is advantageous for the areas of printing plates that correspond to white (blank) areas of the final prints to have maximum water uptake in order to effectively repel the oil-based inks. In addition, the plates must be physically tough in order to resist abrasion. A tradeoff usually exists between these two desirable properties (physical toughness and hydrophilicity).

Imaging compositions for printing plates were formulated using the components and amounts illustrated in TABLE I below. The compositions were coated with a wet coverage of 4.72 cm$^3$/ft$^2$ (51 cm$^3$/m$^2$) on a mechanically grained and anodized aluminum support and dried first in an oven at 80° C. for 5 minutes then for 16 hours at ambient temperature. The toughness of the two coatings was tested for wet abrasion resistance by holding the coatings under a stream of warm tap water for several minutes while scrubbing with a lint free cloth (LYM-TECH Purity Wipe®). All printing plates showed the same results. Only vigorous and sustained scrubbing could remove the coatings. The water uptake of the coatings was measured by swellometry using a commercially available TMA 2740 Thermomechanical analyzer (TA Instruments). The % swelling was measured as a change in the vertical (z) dimension of the coatings upon exposure to water. Coating 1, containing the precursor epoxy compound showed an equilibrium dimension change of 113%. Coatings 2 and 3, prepared using equal coverages of the thiosulfate and sulfonate epoxy compounds showed equilibrium dimension change values of 230% and 245%, respectively, indicating greatly increased water uptake. Thus, the net hydrophilicity of the coatings was increased using the anionic epoxy resins of this invention without a decrease in physical toughness.

TABLE I

| Coating | Epoxy Compound Solution | Wt. resin solution (g) | Polymer solution[2] (g) | Water (g) | Methanol (g) | Surfactant solution[3] (g) | FX-GE-003[4] (g) |
|---|---|---|---|---|---|---|---|
| 1 (control) | DENACOL® EX-521[1] | 0.120 | 7.995 | 7.423 | 7.423 | 0.240 | 1.799 |
| 2 | 1 | 0.609 | 7.995 | 7.179 | 7.179 | 0.240 | 1.799 |
| 3 | 2 | 0.764 | 7.995 | 7.101 | 7.101 | 0.240 | 1.799 |

[1]DENACOL® EX-521 was used neat as received from the manufacturer.
[2]A solution (10.7% in 3:1 methanol:water) of the spiro-quaternary ammonium acrylate switchable polymer

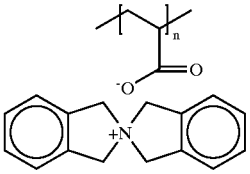

was prepared as described below.
[3]FLUORAD® FC-135 (obtained from 3M), 5% (w/w) in 2:1 isopropanol:water.
[4]FX-GE-003 is an ethanolic PEG-stabilized carbon black dispersion manufactured by Nippon Shokubai.

The spiro-quaternary ammonium acrylate switchable polymer used in the printing plate formulations described above was prepared in the following manner:

A] Anhydrous ammonia (Aldrich) was bubbled through a rapidly stirring suspension of α,α'-dibromo-o-xylene (26.36 g, Aldrich Chemical) in absolute ethanol (300 ml) for 2.5 hours. The reaction mixture was placed in a freezer for 2 hours and then filtered. The collected white solids were washed once with isopropanol and once with diethyl ether to afford 7.95 g of the quaternary ammonium bromide product as fine, white crystals.

B] A sample (7.39 g) of the product from step A was converted from the bromide to the hydroxide using 5.65 g silver (I) oxide and 70 ml of a 9:1 methanol:water mixture in an analogous manner as used for Polymer 6 (Step B). A solution (14.50 g) of 1.452 meq/g of hydroxide anion was obtained.

C] An aqueous solution [5.02 g of a 25% (w/w)] of polyacrylic acid (Polysciences, MW~90,000) was combined with 14.14 g of methanol and 12.00 g of the solution from step B. A gummy precipitate initially formed and was slowly redissolved over 30 minutes. The resulting polymer was stored as a 16% (w/w) solution in a water/methanol mixture.

The compounds of this invention can be used in combination with additional water-soluble or water-dispersible, branched or unbranched compounds that comprise a backbone having covalently attached two or more epoxy moieties and one or more of the same or different organoonium moieties as described in copending and commonly assigned U.S. Ser. No. 10/207,720 filed on even date herewith by Leon, West, and McCovick entitled "Water-Compatible Cationic Epoxy Compounds", which is incorporated herein by reference in preferred embodiments, the organoonium moieties are the same or different organoammonium moieties, the same or different organophosphonium moieties, the same or different organosulfonium moieties, or the same or different N-alkylated, positively charged nitrogen-containing heterocyclic moieties. Thus, such combinations can include one or more anionic compounds and one or more cationic compounds.

The invention has been described in detail with particular reference to certain preferred embodiments thereof, but it will be understood that variations and modifications can be effected within the spirit and scope of the invention.

What is claimed is:

1. A water-soluble or water-dispersible compound having covalently attached thereto two or more epoxy moieties and one or more of the same or different sulfonate or thiosulfate moieties, said compound being derived from a precursor compound represented by either Structure I or II noted below by replacing sufficient epoxy moieties with sulfonates or thiosulfate moieties such that the molar ratio of epoxy moieties to total sulfonates and thiosulfate moieties in said compound is from about 4:1 to about 1:4,

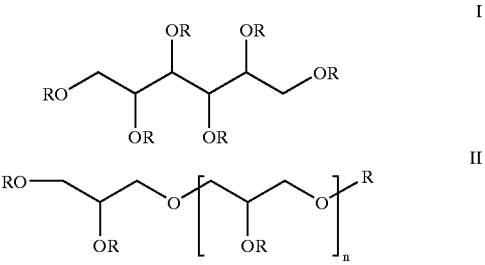

wherein R is hydrogen or a

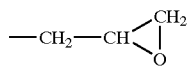

glycidyl moiety, wherein two or more of the R groups in each molecule are glycidyl moieties, wherein n is 1 to 10.

2. The compound of claim 1 wherein said backbone comprises at least 25 weight % oxygen.

3. The compound of claim 1 wherein said backbone comprises from about 30 to about 50 weight % oxygen.

4. A water-soluble or water-dispersible compound comprising a non-aromatic backbone comprising at least 25% by weight of oxygen and the remainder of the weight composed of aliphatic hydrocarbons or halo groups, said compound also having covalently attached to said backbone two or more epoxy moieties and one or more thiosulfate moieties such that the molar ratio of epoxy moieties to thiosulfate moieties in said compound is from about 19:1 to about 1:19.

5. The compound of claim 4 that is derived from a precursor compound represented by the following Structure I or II:

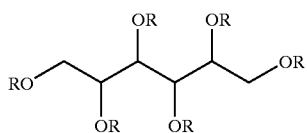
I

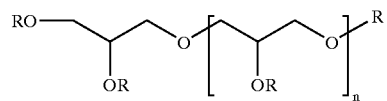
II wherein R is hydrogen or

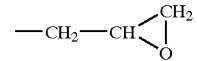

glycidyl moiety, and two or more of the R groups in each molecule are glycidyl moieties, and n is 1 to 10.

* * * * *